US00PP34369P3

(12) United States Plant Patent
Hoekstra

(10) Patent No.: US PP34,369 P3
(45) Date of Patent: Jun. 21, 2022

(54) ***SANSEVIERIA* PLANT NAMED 'OSV SANS 017'**

(50) Latin Name: ***Sansevieria* sp.**
Varietal Denomination: OSV Sans 017

(71) Applicant: ForemostCo., Inc., Miami, FL (US)

(72) Inventor: Folkert Hoekstra, Santa Ana (CR)

(73) Assignee: ForemostCo., Inc., Miami, FL (US)

( * ) Notice: Subject to any disclaimer, the term of this patent is extended or adjusted under 35 U.S.C. 154(b) by 0 days.

(21) Appl. No.: 17/495,919

(22) Filed: Oct. 7, 2021

(65) Prior Publication Data

US 2022/0117141 P1 Apr. 14, 2022

Related U.S. Application Data

(60) Provisional application No. 63/204,558, filed on Oct. 8, 2020.

(51) Int. Cl.
*A01H 5/12* (2018.01)
*A01H 6/12* (2018.01)
*A01H 6/32* (2018.01)

(52) U.S. Cl.
USPC ..... Plt./382
CPC ..... *A01H 6/32* (2018.05)

(58) Field of Classification Search
USPC ..... Plt./382, 383
See application file for complete search history.

(56) References Cited

PUBLICATIONS

Tropicos.org. Missouri Botanical Garden. <https://tropicos.org> retrieved from the Internet Nov. 29, 2021.*

* cited by examiner

*Primary Examiner* — Susan McCormick Ewoldt
(74) *Attorney, Agent, or Firm* — The Webb Law Firm

(57) ABSTRACT

A new and distinct *Sansevieria* plant having dark green and light grey horizontally striped leaves with a thin cream border.

1 Drawing Sheet

Botanical classification: *Sansevieria* sp.
Varietal denomination: 'OSV Sans 017'.

BACKGROUND OF THE INVENTION

The present invention comprises a new and distinct variety of *Sansevieria* plant, having the varietal name of 'OSV Sans 017' and commercially referred to as "Twilight Star". The new variety was discovered and selected by the breeder in a cultivated production bed environment in Williamsburg, Costa Rica as a naturally occurring mutation amongst a population of unpatented and unnamed *Sansevieria* plants. As such, the exact parentage is unknown. The new variety was selected and first asexually reproduced by rhizome cuttings in Williamsburg, Costa Rica. 'OSV Sans 017' has been trial and field tested and has been found to retain its distinctive characteristics and remain true to type through successive propagations. The present invention has not been evaluated under all possible environmental conditions. The phenotype may vary with variations in environment without a change in the genotype of the plant.

When compared to *Sansevieria* variety named 'OSV Sans 004' (U.S. Plant patent application Ser. No. 17/495,477), the new variety exhibits a similar rosette leaf formation with leaves having horizontally stacked lines and a gladiate leaf shape. However, 'OSV Sans 017' differs from 'OSV Sans 004' in having longer leaves with very thin, cream colored margins. Further, the following characteristics distinguish 'OSV Sans 017' from other *Sansevieria* varieties known to the breeder:

Rosette leaf formation;
Very thin, cream colored margins; and
Horizontally stacked and static lines are present across leaves.

DESCRIPTION OF THE DRAWING

The accompanying photographic drawing taken at approximately 18 weeks of age illustrates the new variety, with the colors being as nearly true as is possible with color illustrations of this type.

DESCRIPTION OF THE PLANT

The following detailed description sets forth the characteristics of the new variety at approximately 2 years of age. The data which defines these characteristics was collected in a greenhouse in September of 2021 in Winter Garden, Fla. Plants of the new variety were grown under 2,000 foot candles of artificial light in 15 cm pots in a climate-controlled greenhouse in Winter Garden, Fla. having 86% relative humidity and an average temperature of 28° C. Color references are primarily to the Munsell Plant Tissue Color Book, 2019 publication, except where general color terms are used.

PLANT

Time to initiate roots: About 12 days at an average of 23° C. night temperatures and 30° C. day temperatures.
Time to develop roots: About 21 days at an average of 23° C. night temperatures and 30° C. day temperatures.

Time to produce a finished plant from a rooted cutting: About 8 weeks in a 15 cm container.
Rooting habit and description: Hair-like roots spread out and wrap at the base.
Form: Spreading.
Height from media surface to top of foliage: 16.5 cm.
Plant diameter: 24.8 cm.
Plant shape: Rosette, having a circular arrangement of the leaves.
Vigor: Strong.
Strength: Rigid, with no need for artificial support.
Disease resistance/susceptibility: Nothing specific noted to date.
Pest resistance/susceptibility: Resistant to thrips and aphids.
Temperature tolerance: Sensitive to temperatures below 7° C. or above 38° C.
Drought tolerance: Very tolerant due to the ability of the leaves to retain water.
Flowers: None observed to date.
Seeds/fruit: None present.
Stem:
*Length*.—1.9 cm.
*Diameter*.—2.5 cm.
*Shape*.—Vertical column
*Color*.—2.5GY 8/2.
*Texture*.—Coriaceous and glabrous.
*Strength*.—Sturdy and rigid.
*Internode length*.—Not applicable.
Leaves:
*Arrangement*.—Basal rosette.
*Average number per plant*.—16.
*Length*.—16.6 cm.
*Width*.—7.0 cm.
*Shape of leaf* (*generally*).—Gladiate.
*Shape of apex*.—Apiculate.
*Shape of base*.—Cuneate.
*Margin description*.—Entire.
*Aspect*.—Mostly erect, arching outwardly to about 75°.
*Texture and luster*.—Upper surface: Coriaceous and glabrous. Lower surface: Coriaceous and glabrous.
*Pubescence*.—Upper surface: None present. Lower surface: None present.
*Fragrance*.—None present.
*Color*.—Young leaves: Upper surface: 2.5Y 8/2 margins; 7.5GY 3/2 stacked horizontal lines present on a background of 5GY 4/6. Lower surface: 2.5Y 8/2 margins; 5GY 3/4 stacked horizontal lines present on upper half of leaf and 5GY 4/8 stacked horizontal lines present on lower half of leaf on a background of 5GY 5/8. Mature leaves: Upper surface: 2.5Y 8/2 margins with small lines of 2.5GY 8/2 by margins; 7.5GY 3/2 on top section of leaf; 7.5GY 3/4 on middle section of leaf; 7.5GY 5/6 on bottom section of leaf with a small area of 5Y 8/8; speckles of 5GY 6/6 present throughout leaf. Lower surface: 2.5Y 8/2 margins; 7.5GY 3/2 on top section of leaf; 7.5GY 3/4 on middle section of leaf; 7.5GY 5/6 on bottom section of leaf; small, faint presence of 5Y 8/8 running through center of leaf; speckles of 5Y 6/6 present throughout leaf.
*Veins*.—Venation pattern: Parallel. Color: Upper surface: 5GY 4/6 with 7.5GY 3/2 running through. Lower surface: 5GY 5/8 with 5GY 3/4 and 5GY 4/8 running through.
Sheath:
*Length*.—1.3 cm.
*Width*.—3.8 cm.
*Color*.—5Y 8/2.
*Texture*.—Coriaceous and glabrous.

I claim:

1. A new and distinct variety of *Sansevieria* plant named 'OSV Sans 017', as is herein illustrated and described.

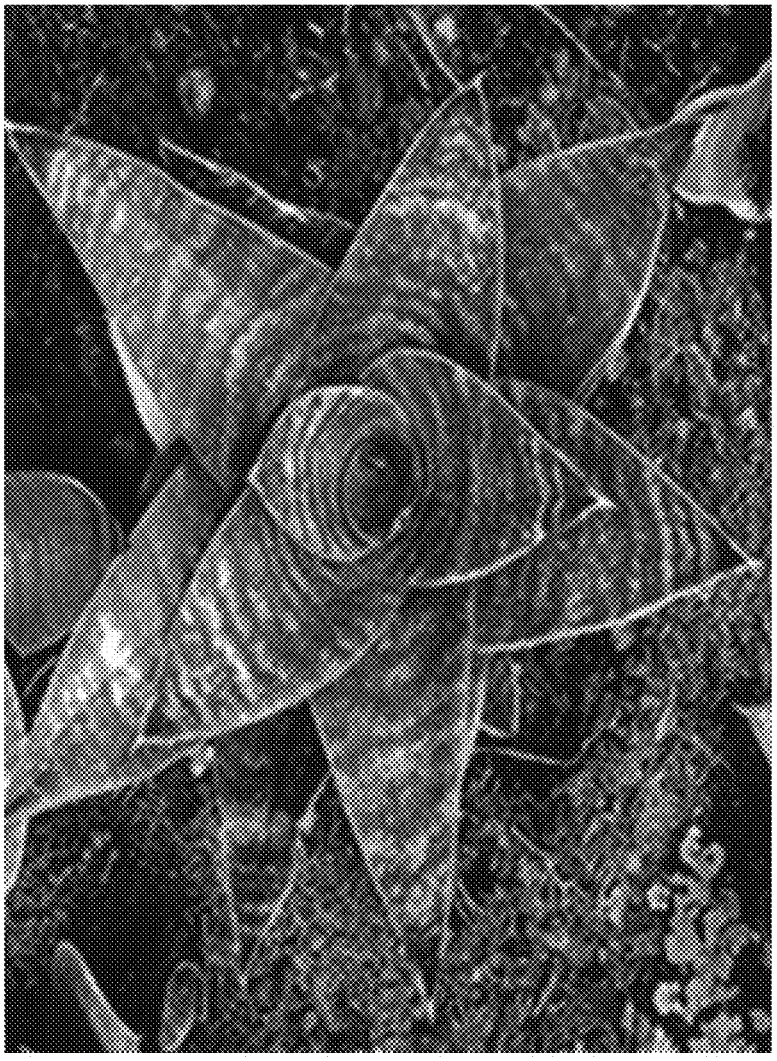

* * * * *